United States Patent [19]

Arenson et al.

[11] Patent Number: 5,076,279

[45] Date of Patent: Dec. 31, 1991

[54] NEEDLE GUIDE FOR ASSEMBLY UPON AN ULTRASOUND IMAGING TRANSDUCER

[75] Inventors: James W. Arenson, Woodside; Douglas M. Bruce, Santa Clara; John J. Cabrall, Pleasanton; Paul E. Cayer, Cupertino; Vaughn R. Marian, Sunnyvale; Jean S. Polinger, Fremont; Richard J. Stevens, San Jose, all of Calif.

[73] Assignee: Acuson Corporation, Mountain View, Calif.

[21] Appl. No.: 553,329

[22] Filed: Jul. 17, 1990

[51] Int. Cl.⁵ .............................................. A61B 10/00
[52] U.S. Cl. .............................. 128/662.05; 128/662.03
[58] Field of Search ...................... 128/662.05, 662.03; 604/116, 117

[56] References Cited

U.S. PATENT DOCUMENTS

| 4,489,730 | 12/1984 | Jingu | 128/662.05 |
| 4,491,137 | 1/1985 | Jingu | 128/662.05 |
| 4,576,175 | 3/1986 | Epstein | 128/662.05 |
| 4,688,578 | 8/1987 | Takano et al. | 128/662.03 |
| 4,898,178 | 2/1990 | Wedel | 128/754 |

Primary Examiner—Francis Jaworski
Assistant Examiner—Scott R. Akers
Attorney, Agent, or Firm—James F. Mitchell

[57] ABSTRACT

A biopsy needle guide for assembly with an ultrasound imaging transducer including a transducer nosepiece and a needle guide having at least one set of alignment means and a spring means for securing the needle guide to the transducer nosepiece while simultaneously stretching and holding a sterile cover over the face of the transducer.

8 Claims, 4 Drawing Sheets

NEEDLE GUIDE FOR ASSEMBLY UPON AN ULTRASOUND IMAGING TRANSDUCER

BACKGROUND OF THE INVENTION

Needle guide adapters for mounting upon ultrasound imaging transducers are known in the prior art for guiding biopsy needles into puncturing engagement and insertion into a patient within the plane of an ultrasound image. Usual procedure includes covering the transducer face with a sterile latex cover usually provided with integral or separate ties to hold the protective cover over the transducer face. Prior art guides have bulky mechanical components with obtrusive hardware that interferes with free access of the transducer on the patient. Prior needle guides have been difficult to align and mount on the transducer and generally did not by themselves hold or stretch the cover over the transducer face.

SUMMARY OF THE INVENTION

This invention is a needle guide which may be precisely, quickly and easily assembled to an ultrasound imaging transducer and which automatically stretches and holds in place a sterile protective cover over the transducer face. The improved guide requires unobtrusive alignment details on the nosepiece of the ultrasound imaging transducer which add no bulk to it and enable easy access to image the patient with or without the needle guide assembled. At least one set of a groove or other recess and a mating protrusion on one or the other of the transducer nosepiece and needle guide align the two components. These alignment means have rounded edges and are shallow so that they are easily cleaned of acoustic gel. The needle guide, thus, becomes self-locating and is tolerant of slight misalignment as the guide and transducer are assembled. The guide will mount to the transducer nosepiece only when correctly aligned and will positively latch in place only when correctly mounted. The needle guide stretches a sterile protective cover over the transducer face and spring means holds the cover in place by a press-fit between the needle guide and transducer nosepiece. The spring means enables assembly with less force than is required to disassemble. Alignment of the needle guide is referenced to the edge of the transducer array at one side of the nosepiece to reduce tolerance stacked up in the assembly and to yield better alignment within the scanning plane.

DESCRIPTION OF A PREFERRED EMBODIMENT

Figure 1:
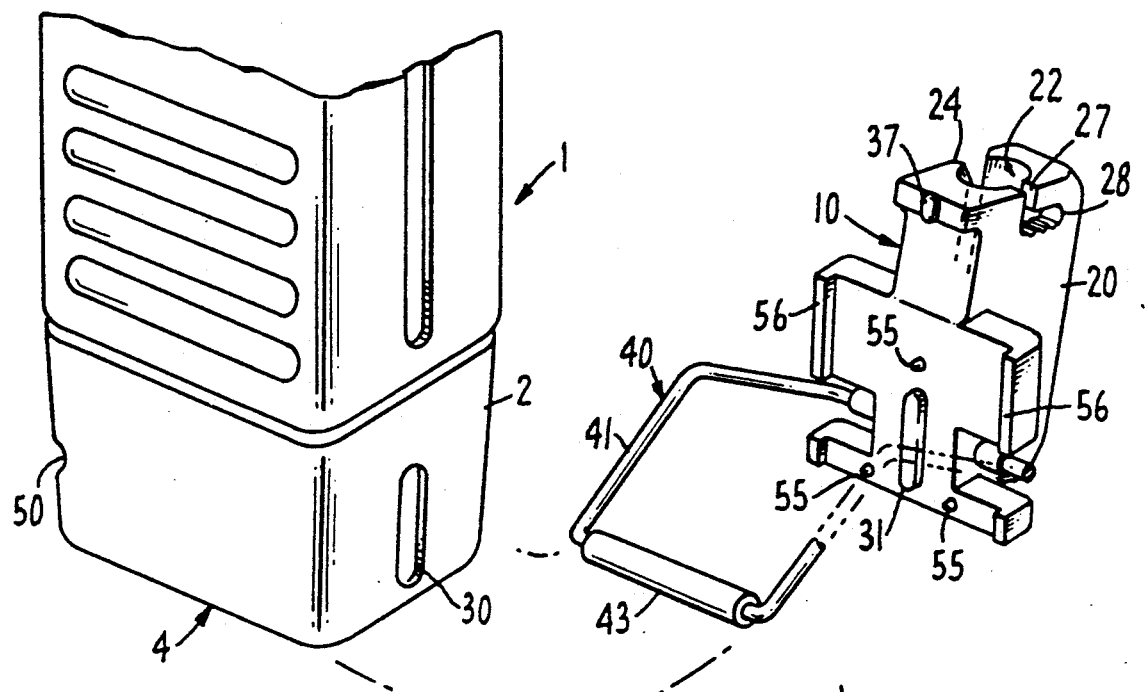
FIG. 1 is an exploded perspective view of the disassembled ultrasound imaging transducer, needle guide and sterile protective cover.
Figure 2:
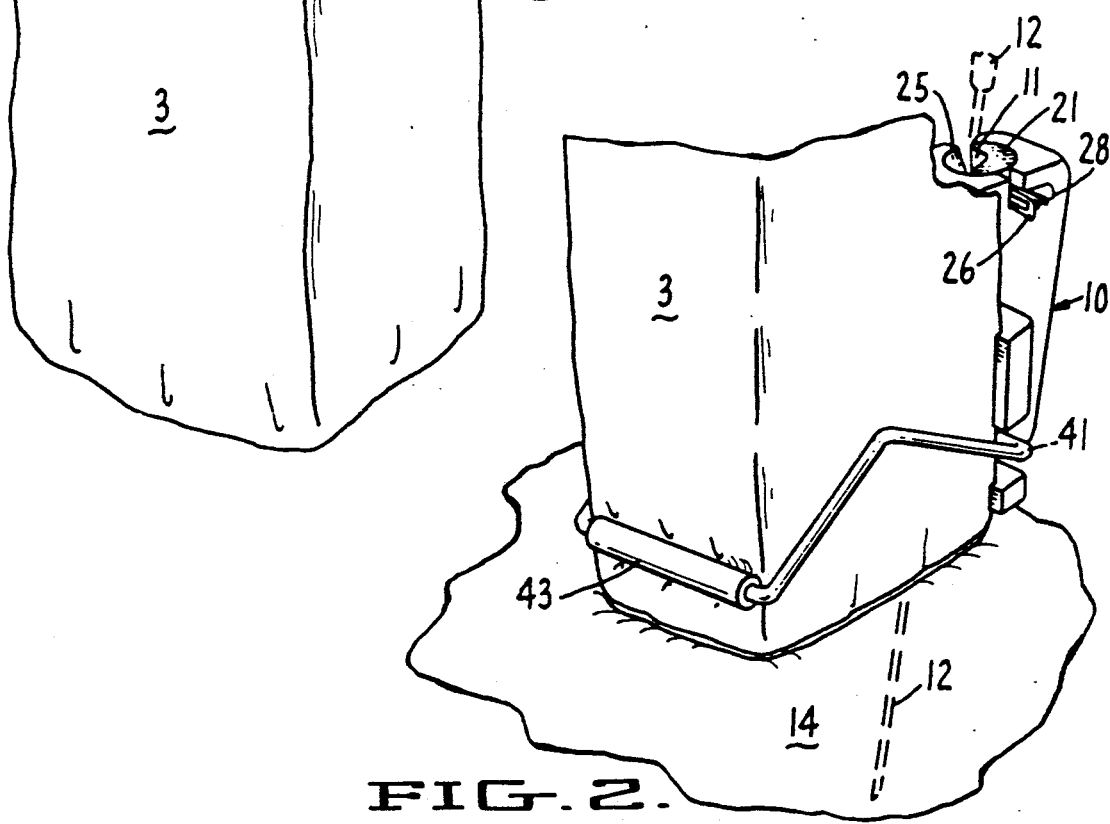
FIG. 2 is a perspective view of the assembled needle guide, ultrasound imaging transducer and protective cover applied to the skin of a patient.
Figure 3:
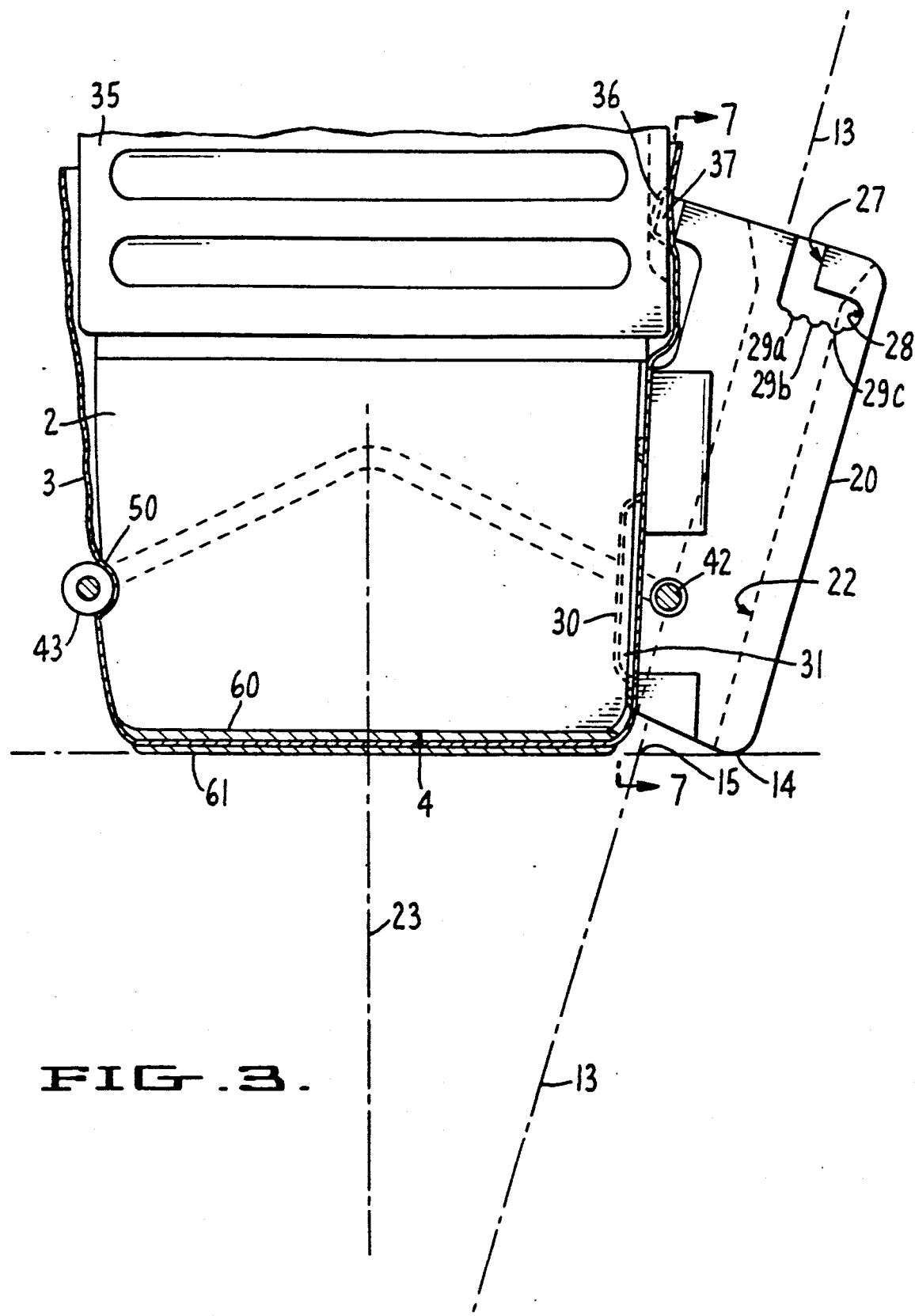
FIG. 3 illustrates, partly in section, the needle guide mounted upon the nosepiece of the ultrasound imaging transducer and the simultaneous stretching and holding of the protective cover in place.

FIG. 1 illustrates an ultrasound imaging transducer referred to generally as 1 having a nosepiece 2. A sterile protective cover 3 usually of latex or similar material, which may either be a closed sleeve or a flat piece of material, is stretched over the face of the transducer 4 and held in place by needle guide 10, as shown in FIG. 2. As shown in FIGS. 2 and 3, the needle guide 10 has a through guide slot 11 which receives and guides a biopsy needle 12 for exit along the guide slot axis 13 to enable puncture of the patient's skin 14 as at 15 and permit insertion into the patient along an extension of the guide slot axis 13.

Figure 9:
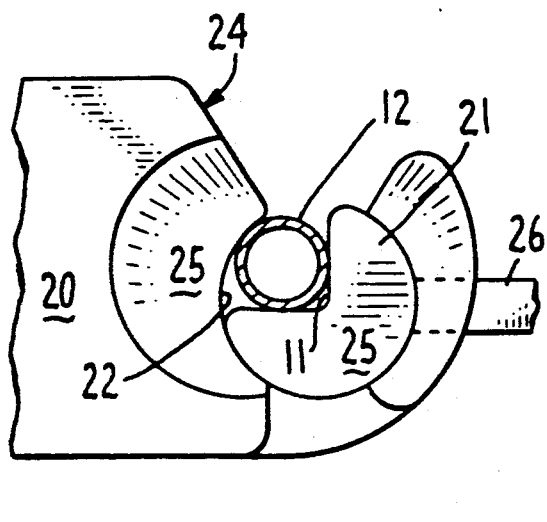
FIG. 9 is a top view, partly in section, of a portion of the needle guide, insert pin and needle in a closed position.
Figure 10:
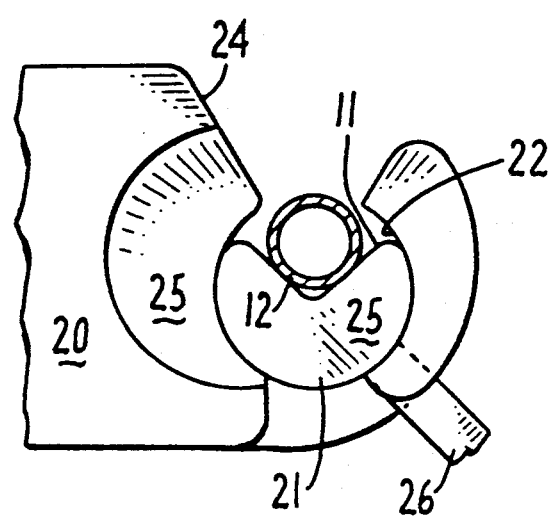
FIG. 10 is a top view, partly in section, of that portion of the needle guide, insert pin and needle in an open position.

The needle guide includes a body 20 in which the needle guide slot 11 may be defined by one of a plurality of insert pins 21 having its guide slot 11 sized to accommodate the usual range of biopsy needle sizes between thirteen and twenty-two gauge, for example. As is known in the prior art, the selected insert pin 21 fits within a pin bore 22 in the needle guide body 20 oriented at an angle relative to a line 23 normal to the face 4 of the transducer array. When the insert pin 21 is latched in a closed position in the needle guide body 20, the needle is captured within the insert pin guide slot 11 by the wall of the pin bore 22 as illustrated in FIG. 9. When the insert pin 21 is rotated to an open position, as in FIG. 10, the insert pin guide slot 11 aligns with a corresponding discharge slot 24 in the needle guide body 10, allowing the needle 12 to fall out of the insert pin 21 and needle guide. In this way the needle 12 can be decoupled quickly from the needle guide even while the needle 12 remains in a patient.

Figure 8:
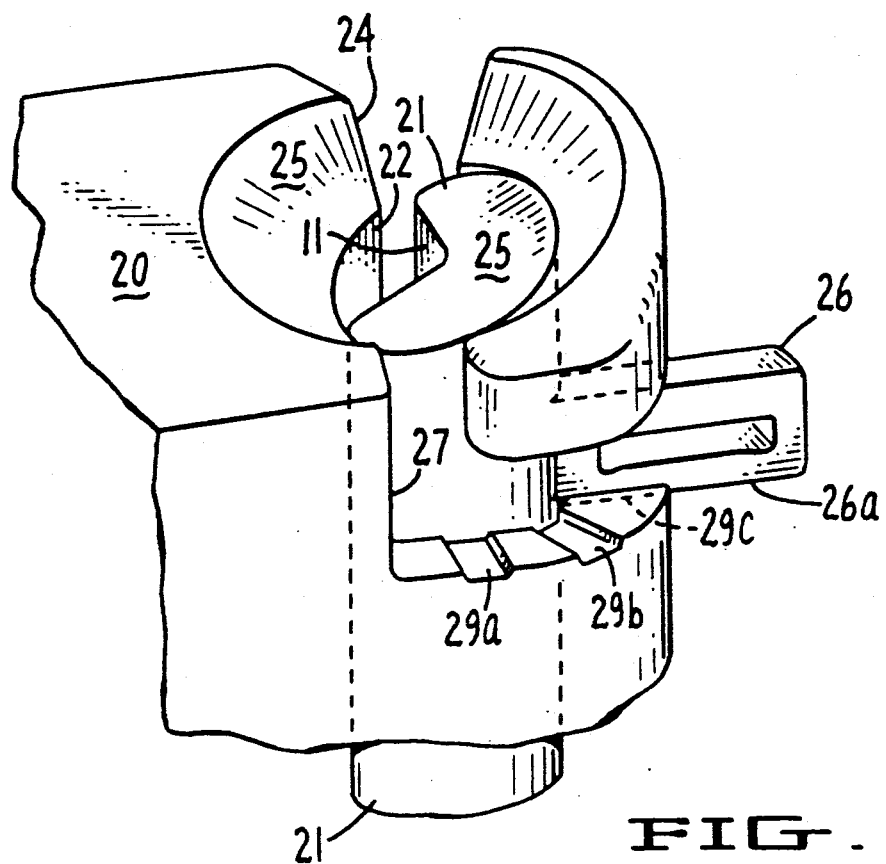
FIG. 8 is a perspective view of the top of an insert pin useful with the needle guide of this invention.

The insert pin 21 and needle guide body may have a funnel-shaped depression 25, as is shown in FIGS. 8,9, centered on the insert pin guide slot 11 to aid in inserting a needle into the guide slot. The insert pin 21 may also have a protruding lever 26 which fits within a L-shaped slot 27 in the needle guide. The insert pin is secured in the pin bore 22 by a slight twist of the insert pin 21 to engage the lever 26 within a latching portion 28 of the L-shaped slot 27, as shown in FIGS. 2 and 3. The lower margin 29 of the latching portion 28 of the L-shaped slot 27 has three detents 29a-c to receive the lever 26 and latch it in three discrete positions; closed with needle ready for use at detent 29c, open for quick release of the needle through slot 24 in the needle guide at detent 29a and an intermediate position at detent 29b for inserting or removing the insert pin-needle assembly from the needle guide. The lower edge 26a of the lever has flexure to securely latch the lever 26 at the several detent positions.

In the described embodiment, the nosepiece 2 of the ultrasound imaging transducer 1 carries a vertical recess or groove 30 which mates with a corresponding vertical protrusion or ridge 31 in the needle guide body 20 of commensurate shape and length. The ultrasound imaging transducer body 35, itself, in the described embodiment has a vertical guide slot 36 above the recess 30 on the nosepiece 2 which receives a guide protrusion 37 on the needle guide body 20 as the needle guide 10 is slipped upwardly and assembled to the nosepiece 2 and transducer body 35. This slot and protrusion combination aids in positioning the needle guide vertically on the correct side of the nosepiece 2.

The needle guide 2 is held in place in pressing engagement with the imaging transducer 1 by spring means 40 which in the described embodiment is a generally U-shaped bent wire 41 pivotable at both ends 42 upon the needle guide body 20 and carrying at its distal or free end a roller 43 which during assembly rolls upwardly upon the nosepiece 2 into engagement with a second horizontal recess or groove 50 on the nosepiece 2. The recesses or grooves 30,50 on the nosepiece are at right angles to one another so that the roller 43 and ridge 31 can mount only upon the proper side of the nosepiece.

Figure 4:
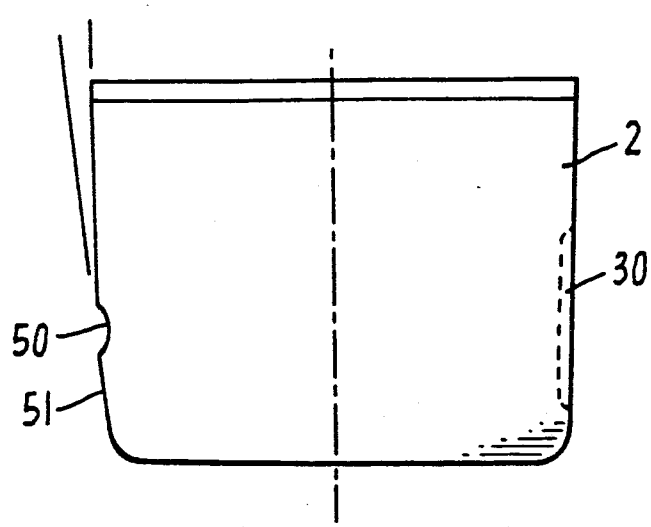
FIG. 4 is an elevational view of one end of the nosepiece of the ultrasound imaging transducer.
Figure 5:
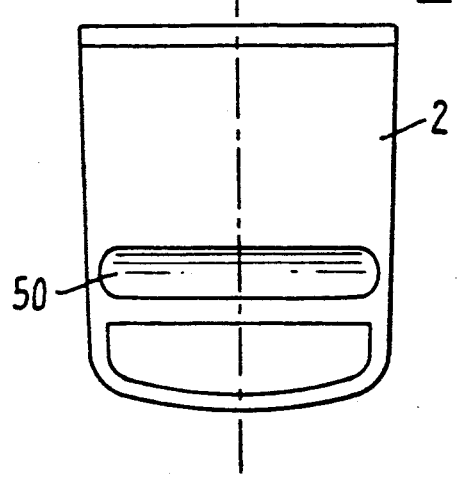
FIG. 5 is an elevational view of one side of the nosepiece of the ultrasound imaging transducer.
Figure 6:
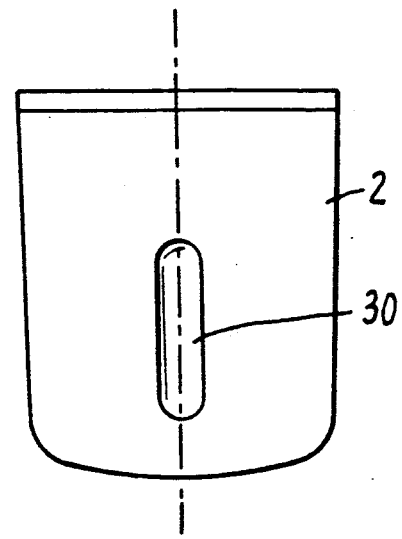
FIG. 6 is an elevational view of the opposite or guide mounting side of the ultrasound imaging transducer.
Figure 7:
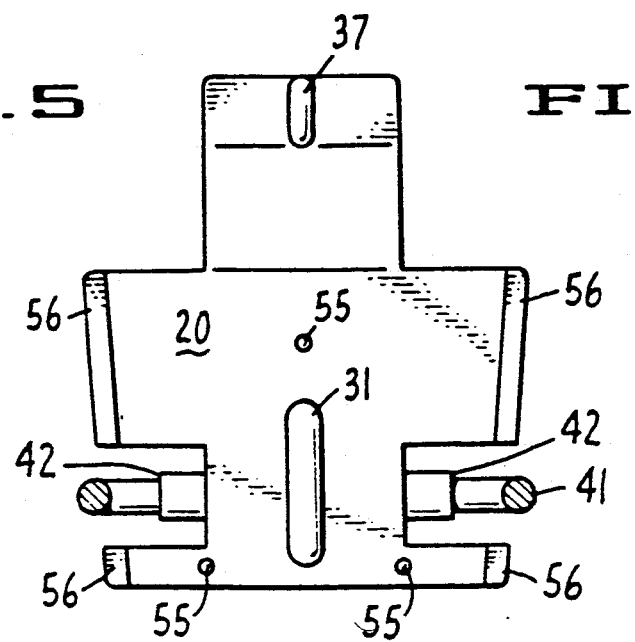
FIG. 7 is an elevational view of the needle guide face which mounts against the nosepiece of the ultrasound imaging transducer taken along line 7—7 of FIG. 3.

The needle guide 10 and its mounting spring means 40 hold in place the sterile protective cover 3 over the transducer face 4, as shown in FIGS. 2 and 3. The pressing engagement of the spring roller 43 moving along the nosepiece 2 smoothes out the cover and stretches it over the transducer face. The bent wire type of spring means provides a spring loading as the spring means is mounted upon and rolled upwardly on the generally diverging nosepiece sides as at 51 in FIG. 4. The spring straightens slightly as the roller clears the face 4 of the transducer and moves upwardly. The length, stiffness and axis of rotation 42 of the spring means 41 as well as the related groove 50 in the nosepiece are designed to inhibit assembly of the needle guide to the transducer unless the needle guide is mounted on the correct side of the nosepiece with its ridge 31 approximately within vertical groove 30. Thus, the guide will not go on the transducer unless alignment is approximately correct. Secondly, the roller 43 moves onto the nosepiece more easily than it will move off in order to assure easy assembly with more difficult disassembly, accidentally or otherwise. The applied spring force is sufficient to hold the needle guide in place and stretch out and compress any creases in the cover that may fall under the mating grooves, protrusions and the guide, itself.

A set of three or more protrusions 55 around the vertical ridge 31 on the face of the noseguide which mounts against the transducer minimizes the likelihood of locating the needle guide 10 on top of a crease in the protective cover 3. Concentration of the pressure between needle guide 10 and nosepiece 2 tends to flatten out creases in the cover 3 which may lie over the transducer face 4 or fall under a protrusion. The set of protrusions 55 also forms a stable multi-point base upon which the needle guide rests against the nosepiece regardless of the relative flatness of their two mating surfaces.

Wings 56 at the margins of the mating face of the needle guide body 20 are positioned to limit the travel of spring means 40 and to aid in aligning the needle guide on the transducer during assembly.

In order to assemble the components, an operator first applies acoustic coupling gel 60 to the transducer face as indicated in FIG. 3. The sterile protective cover 3 is then applied over the transducer 1. The needle guide 2 then is placed against the side of the transducer so that the groove 30 and ridge 31 are mated. The bent wire spring means 41 with its roller 43 is then pivoted over the face 4 of the transducer to its far edge, then pivoted upwardly on the side of the transducer nosepiece remote from the needle guide until the roller 43 is located in horizontal groove 50. Gel 61 is then applied to the outside of the protective cover at the transducer face 4. The imaging transducer is placed upon the patient's skin 14, as in FIGS. 2 and 3, and imaging can proceed. To remove the needle guide the operator pushes the roller 43 and wire 41 pivotally downward towards the transducer face. As the roller comes out of the groove 50 and clears the face of the transducer, the needle guide 10 falls away.

Various modifications of the described embodiment may be apparent. The needle guide may be fabricated from steel so as to be reusable after sterilization. However, the body could be made out of a variety of materials such as plastic for ease of manufacture and as a low cost disposable unit. The spring means may be steel wire and could be in a variety of shapes and materials while still preserving the concept of a spring biasing means which is pivotable over the transducer face into the retaining recess 50 on the transducer nosepiece. A properly contoured spring means could be used instead of roller 43. The seating protrusions 55 can be in a variety of sizes and location while still maintaining their described function or they could be protruding ridges. As described, the grooves in the nosepiece and the related protrusions on the needle guide and spring means are sized respectively to accommodate the sterile protective cover embraced between them. The horizontal groove 50 which captures the spring means roller 43 may be with or without a ramp 51 to the transducer face 4. Various other modifications will be apparent to those familiar with the needle guide art for ultrasound imaging transducers.

We claim:

1. An assembly of a biopsy needle guide and ultrasound imaging transducer, comprising
   an ultrasound imaging transducer with a nosepiece having a generally rectangular transducer face at its distal end, and having smooth side walls extending away from said transducer face, said nosepiece having a first side with first and second locating recesses, said first recess being adjacent said transducer face and the second recess spaced further away from said transducer face, and an opposite second side having a locating groove;
   a biopsy needle guide adapted to be removably connected to the first side of the nosepiece and having a first locating protrusion means adjacent to the transducer face for mating with said first locating recess and having a second locating protrusion means for mating with said second locating recess; and
   spring means for securing the needle guide to the transducer nosepiece, said spring means being attached to the needle guide and being pivotable into releasable abutment with said locating groove on said second side of the nosepiece remote from said needle guide.

2. The apparatus of claim 1 further comprising a sterile protective cover stretched and held over the transducer face of said nose-piece by pressing abutment of said needle guide and spring means against said nosepiece.

3. The apparatus of claim 1 wherein said biopsy needle guide has a guide slot for receiving and guiding a biopsy needle to exit the slot adjacent to the transducer face.

4. The apparatus of claim 1 wherein said spring means comprises a bent wire spring which straightens slightly against spring tension upon being press-fit into said locating groove.

5. The apparatus of claim 1 wherein said first locating recess is perpendicular to said locating groove.

6. The apparatus of claim 1 further comprising
a cylinder pin bore formed in said needle guide,
a discharge slot formed in said needle guide which connects with said cylindrical pin bore,
an insert pin carried by said pin bore, said insert pin having a guide slot which slidably receives a biopsy needle, and
lever means for rotating said insert pin to a first position wherein a biopsy needle is captured within said guide slot, or to a second position wherein said guide slot aligns with said discharge slot so a biopsy needle may pass through said discharge slot and may be separated completely from the needle guide even while the needle remains in a patient.

7. The apparatus of claim 2 wherein the bent wire spring carries a roller which rolls against and stretches said protective cover, and press-fits into said locating groove to latch the needle guide and transducer nosepiece together.

8. The apparatus of claim 3 wherein an extension of the axis of said guide slot is at an angle to a normal to the transducer face and within the scanning plane of the imaging transducer.

* * * * *